US006943692B2

(12) United States Patent
Castner et al.

(10) Patent No.: US 6,943,692 B2
(45) Date of Patent: Sep. 13, 2005

(54) APPARATUS AND METHODS FOR ON-LINE MONITORING OF FLUORINATED MATERIAL IN HEADSPACE OF VIAL

(75) Inventors: James Castner, Groton, MA (US); Luc Boudreau, Val Belair, CA (US); Allan Rilling, Les Saules, CA (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 336 days.

(21) Appl. No.: 10/062,206

(22) Filed: Feb. 1, 2002

(65) Prior Publication Data

US 2003/0087445 A1 May 8, 2003

Related U.S. Application Data

(60) Provisional application No. 60/265,919, filed on Feb. 2, 2001.

(51) Int. Cl.$^7$ .............................................. G08B 17/10
(52) U.S. Cl. ..................... 340/632; 340/600; 340/674; 209/3.2; 209/524; 209/582; 209/588; 356/240.1; 356/338
(58) Field of Search ............................. 340/600, 632, 340/674; 209/3.1, 3.2, 524, 581, 582, 588; 356/240.1, 338, 443, 448, 240

(56) References Cited

U.S. PATENT DOCUMENTS

| | | | |
|---|---|---|---|
| 3,608,715 A | 9/1971 | Snyder et al. ............... 209/590 |
| 4,300,689 A | 11/1981 | Franklin et al. ............ 209/524 |
| 4,368,980 A | 1/1983 | Aldred et al. ............. 359/269.4 |
| 4,651,879 A | 3/1987 | Harris et al. ................. 209/523 |
| 4,971,900 A | * 11/1990 | Ahnell et al. .................. 435/29 |
| 5,067,616 A | 11/1991 | Plester et al. ................ 209/3.1 |
| 5,155,019 A | 10/1992 | Sussman et al. ............... 435/34 |
| 5,305,887 A | 4/1994 | Krieg et al. .................. 209/3.1 |
| 5,350,565 A | 9/1994 | Leveson et al. .............. 422/64 |
| 5,361,912 A | 11/1994 | Krieg et al. ................. 209/524 |
| 5,465,822 A | 11/1995 | DeWoolfson et al. ....... 194/209 |
| 5,614,718 A | * 3/1997 | Brace .................. 250/339.136 |
| 5,769,080 A | 6/1998 | Unger et al. ................. 600/458 |
| 6,395,538 B1 | * 5/2002 | Naughton et al. ........ 435/288.7 |
| 2003/0111607 A1 | * 6/2003 | Bachur et al. .............. 250/343 |

FOREIGN PATENT DOCUMENTS

EP  0030630742  * 3/1989  .......... G01N/33/44

OTHER PUBLICATIONS

H. Martens et al., Multivariate Calibration (1989)John Wiley & Sons, p. 188.
H. Martenset al., Multivariate Calibration (1989) John Wiley & Sons, p. 188.

* cited by examiner

Primary Examiner—Benjamin C. Lee
(74) Attorney, Agent, or Firm—Jennifer T. Chin (57) ABSTRACT

Apparatus and methods for monitoring the presence of an analyte in a closed vial wherein a sample contained within the closed vial is conveyed to an analyzer. The analyzer determines a value of a spectral property dependent on analyte concentration at a position within a headspace formed above the sample within the vial. An indicator is used to compare the measured value of the spectral property with a predetermined limit criteria to determine the presence or absence of the analyte. Vials wherein the presence of the analyte is detected are indicated as product vials whereas vials wherein the absence of the analyte is detected are indicated as rejected vials. The rejected vials are conveyed by a transferrer to a rejected vial station. A first portion of the product vials are conveyed by a sampler to a sample collection station. A second portion of the product vials are conveyed to a labeler.

50 Claims, 3 Drawing Sheets

APPARATUS AND METHODS FOR ON-LINE MONITORING OF FLUORINATED MATERIAL IN HEADSPACE OF VIAL

FIELD OF THE INVENTION

The present invention relates to apparatus and methods for the on-line monitoring of gas in the headspace of a vial and, in particular, to apparatus and methods for the on-line monitoring of fluorinated material in the headspace of a pharmaceutical vial using infrared (IR) spectroscopy.

BACKGROUND OF THE INVENTION

Ultrasound is a diagnostic imaging technique which provides a number of advantages over other diagnostic methodology. Unlike techniques such as nuclear medicine and X-rays, ultrasound does not expose the patient to potentially harmful exposures of ionizing electron radiation that can potentially damage biological materials, such as DNA, RNA, and proteins. In addition, ultrasound technology is a relatively inexpensive modality when compared to such techniques as computed tomography (CT) or magnetic resonance imaging.

The principle of ultrasound is based upon the fact that sound waves will be differentially reflected off of tissues depending upon the makeup and density of the tissue or vasculature being observed. Depending upon the tissue composition, ultrasound waves will either dissipate by absorption, penetrate through the tissue, or reflect back. Reflection, referred to as back scatter or reflectivity, is the basis for developing an ultrasound image. A transducer, which is typically capable of detecting sound waves in the range of 1 MHz to 10 MHz in clinical settings, is used to sensitively detect the returning sound waves. These waves are then integrated into an image that can be quantitated. The quantitated waves are then converted to an image of the tissue being observed.

Despite technical improvements to the ultrasound modality, the images obtained are still subject to further refinement, particularly in regards to imaging of the vasculature and tissues that are perfused with a vascular blood supply. Toward that end, contrast agents are typically used to aid in the visualization of the vasculature and vascular-related organs. In particular, microbubbles or vesicles are desirable as contrast agents for ultrasound because the reflection of sound at an interface created at the surface of a vesicle is extremely efficient. It is known to produce suitable contrast agents comprising microbubbles by first placing an aqueous suspension (i.e., a bubble coating agent), preferably comprising lipids, into a vial or container. A gas phase is then introduced above the aqueous suspension phase in the remaining portion, or headspace, of the vial. The vial is then shaken prior to use in order to form the microbubbles. It will be appreciated that, prior to shaking, the vial contains an aqueous suspension phase and a gaseous phase. A wide variety of bubble coating agents may be employed in the aqueous suspension phase. Likewise, a wide variety of different gases may be employed in the gaseous phase. In particular, however, perfluorocarbon gases such as perfluoropropane may be used. See, for example, Unger et al., U.S. Pat. No. 5,769,080, the disclosure of which is hereby incorporated in by reference in its entirety.

In practice, vials containing the aqueous suspension and gas phases are prepared and sealed, significantly before use, for shipment. It would be highly beneficial to provide apparatus and methods for quickly and non-invasively detecting the presence or absence of the gas phase in the headspace of the sealed vial. The apparatus and methods should be able to determine the presence or absence of one or more specific gases, such as perfluorocarbons, including perfluoropropane (PFP), and should be accurate and robust. Further, the apparatus and methods should be practical for a manufacturing application and, in particular, should afford a low cost per analysis, simplicity of use, and a fast sample through-put rate.

SUMMARY OF THE INVENTION

The present invention provides apparatus and methods for quickly and non-invasively detecting the presence or absence of specific fluorinated gases, such as perfluorocarbons, including perfluoropropane, in the headspace of sealed vials. The apparatus and methods are accurate, robust, and practical for manufacturing applications. In particular, the present invention affords low cost per analysis, simplicity of use, and fast sample through-put rates.

In one of its aspects, the present invention relates to apparatus for monitoring the presence of an analyte in a closed vial. The apparatus comprises a conveyor operatively associated with a vial feeding mechanism for receiving vials from the vial feeding mechanism. A transporter is optionally provided between the vial feeding mechanism and the conveyor for receiving vials from the vial feeding mechanism and transferring vials to the conveyor. A first vial counter operatively associated with the transporter for counting the number of vials received by the transporter. An analyzer is operatively associated with the conveyor for determining a value of a spectral property at a position within the headspaces of vials. In particular, the analyzer determines the value of a spectral property that is dependent upon analyte concentration. An indicator is operatively associated with the analyzer and the conveyor for indicating vials wherein the presence of the analyte is detected as product vials and for indicating vials wherein the absence of the analyte is detected as rejected vials. Also, the system can identify whether the spectum or signal is good or bad. For example, when there is a misalignment of the vials, you will have an inaccurate signal (i.e. a bad signal) reported by unit (19) and the vial would then be rejected. A transferrer is optionally provided for receiving vials from the conveyor and transferring the rejected vials to a reject station. A second vial counter is optionally operatively associated with the transferrer for counting the number of vials received by the transferrer. An optional sampler is operatively associated with the transferrer for removing a portion of the product vials from the transferrer and transferring those vials to a sample collection station. A third vial counter is optionally operatively associated with the sampler for counting the number of vials received by the sampler. An optional labeler is operatively associated with the transferrer for labeling product vials received from the transferrer. Alternatively, product vials can be transferred from the transferrer to a product collection station. A fourth vial counter is operatively associated with the transferrer for counting the number of vials transferred from the transferrer to the product collection station.

In another of its aspects, the present invention relates to methods for monitoring the presence or absence of an analyte in a closed vial. A sample contained within a closed vial is conveyed to an analyzer. The analyzer determines a value of a spectral property dependent on analyte concentration at a position within a headspace formed above the sample within the vial. The measured value of the spectral property is compared with a predetermined limit criteria to determine the presence of the analyte. Vials wherein the presence of the analyte is detected are indicated as product vials, whereas vials wherein the absence of the analyte is detected are indicated as rejected vials. The rejected vials are conveyed to a rejected vial station. A first portion of the product vials are conveyed to a sample collection station and the remainder of the product vials are conveyed to a labeler.

In yet another of its aspects, the present invention relates to methods for monitoring the presence or absence of an analyte in a headspace of a sample vial. A first spectral analysis is performed on an analyte contained within a headspace of a test vial, wherein the concentration of the analyte in the headspace is at a predetermined level. A spectral region containing an absorption peak specific for the analyte in the headspace of the test vial from the first spectral analysis is then identified. In one embodiment, the spectral region includes an infrared spectral region. A first intensity for the identified spectral region from the first spectral analysis is determined. A second spectral analysis is performed on gas contained within a headspace of a sample vial containing a sample. A second intensity for the identified spectral region from the second spectral analysis is then determined and compared with the first intensity to determine the presence or absence of analyte in the headspace of the sample vial. In one embodiment, the first and second intensities are determined from a height of the absorption peak. Alternatively, the first and second intensities are determined from an area of the absorption peak using, for example, a partial least squares algorithm or a peak height algorithm.

Furthermore, in yet another of its aspects, the present invention relates to methods for quantitatively measuring analyte in a headspace of a sample vial. A first spectral analysis is performed on an analyte contained within a headspace of a test vial, wherein the concentration of the analyte in the headspace is at a predetermined level. A spectral region containing an absorption peak specific for the analyte in the headspace of the test vial from the first spectral analysis is then identified. In one embodiment, the spectral region includes an infrared spectral region. A first intensity for the identified spectral region from the first spectral analysis is determined. A second spectral analysis is performed on gas contained within a headspace of a sample vial containing a sample. A second intensity for the identified spectral region from the second spectral analysis is then determined and compared with the first intensity to determine the quantitative amount of analyte in the headspace of the sample vial. In one embodiment, the first and second intensities are determined from a height of the absorption peak. Alternatively, the first and second intensities are determined from an area of the absorption peak using, for example, a partial least squares algorithm or a peak height algorithm.

DETAILED EMBODIMENTS OF THE INVENTION

[1] In a first embodiment, the present invention relates to an apparatus for monitoring the presence of an analyte in a closed vial comprising:
 1. a vial feeding mechanism;
 2. a conveyor operatively associated with the vial feeding mechanism for receiving vials from the vial feeding mechanism;
 3. an analyzer operatively associated with the conveyor for determining a value of a spectral property at a position within headspaces of the vials, the spectral property being dependent on analyte concentration; and
 4. an indicator operatively associated with the analyzer and the conveyor for indicating vials wherein the presence of the analyte is detected as product vials and for indicating vials wherein the absence of the analyte is detected as rejected vials.

[2] In another embodiment, the present invention relates to embodiment [1] further comprising a transporter operatively associated with the vial feeding mechanism for receiving vials from the vial feeding mechanism and operatively associated with the conveyor for transferring vials to the conveyor.

[3] In another embodiment, the present invention relates to either embodiment [1] or [2] further comprising a first vial counter operatively associated with the transporter for counting the number of vials received by the transporter.

[4] In another embodiment, the present invention relates to any one of embodiments [1], [2] or [3], further comprising a transferrer for receiving vials from the conveyor.

[5] In another embodiment, the present invention relates to any one of embodiments [1], [2], [3] or [4], further comprising a reject station operatively associated with the transferrer for receiving rejected vials from the transferrer.

[6] In another embodiment, the present invention relates to any one of embodiments [1], [2], [3], [4] or [5], further comprising a second vial counter operatively associated with the transferrer for counting the number of vials received by the transferrer.

[7] In another embodiment, the present invention relates to any one of embodiments [1] to [6], further comprising a sampler operatively associated with the transferrer for removing sample collection vials from the transferrer.

[8] In another embodiment, the present invention relates to any one of embodiments [1] to [7], further comprising a third vial counter operatively associated with the sampler for counting the number of vials received by the sampler.

[9] In another embodiment, the present invention relates to any one of embodiments [1] to [8], further comprising a sample collection station operatively associated with the sampler for receiving the sample collection vials from the sampler.

[10] In another embodiment, the present invention relates to any one of embodiments [1] to [9], further comprising a labeler operatively associated with the transferrer for labeling product vials received from the transferrer.

[11] In another embodiment, the present invention relates to any one of embodiments [1] to [6], wherein the analyte comprises a perfluorocarbon gas.

[12] In another embodiment, the present invention relates to embodiment [11] wherein the perfluorocarbon gas comprises perfluoropropane.

[13] In another embodiment, the present invention relates to any one of embodiments [1] to [12], further comprising a separator situated between the vials on the conveyor, such that the signal from the analyzer does not saturate the indicator as the vials are moved through the optical path of the analyzer.

[14] In another embodiment, the present invention relates to a method for monitoring the presence of an analyte in a closed vial comprising the steps of:
 1. conveying a sample contained within the closed vial to an analyzer;
 2. determining a value of a spectral property dependent on analyte concentration at a position within a headspace formed above the sample within the vial;
 3. comparing the measured value of the spectral property with a predetermined limit criteria to determine the presence of the analyte;

4. indicating vials wherein the presence of the analyte is detected as product vials and indicating vials wherein the absence of the analyte is detected as rejected vials;
5. conveying the rejected vials to a rejected vial station;
6. conveying a first portion of the product vials to a sample collection station; and
7. conveying a second portion of the product vials to a labeler.

[15] In another embodiment, the present invention relates to embodiment [14] wherein the analyte comprises a perfluorocarbon gas.

[16] In another embodiment, the present invention relates to embodiment [15] wherein the perfluorocarbon gas comprises perfluoropropane.

[17] In another embodiment, the present invention relates to a method for monitoring the presence of an analyte in a headspace of a sample vial comprising the steps of:
1. performing a first spectral analysis of an analyte contained within a headspace of a test vial, wherein the concentration of the analyte in the headspace is at a predetermined level;
2. identifying a spectral region containing an absorption peak specific for the analyte in the headspace of the test vial from the first spectral analysis;
3. determining a first intensity for the identified spectral region from the first spectral analysis;
4. performing a second spectral analysis of gas contained within a headspace of a sample vial containing a sample;
5. determining a second intensity for the identified spectral region from the second spectral analysis;
6. comparing the second intensity with the first intensity to determine the presence of the analyte in the headspace of the sample vial.

[18] In another embodiment, the present invention relates to embodiment [17] wherein the spectral region identified is an infrared spectral region.

[19] In another embodiment, the present invention relates to any one of embodiments [17] to [18], wherein the first and second intensities are determined from a height of the absorption peak.

[20] In another embodiment, the present invention relates to any one of embodiments [17] to [19], wherein the first and second intensities are determined from an area of the absorption peak.

[21] In another embodiment, the present invention relates to any one of embodiments [17] to [20], wherein the area of the absorption peak is determined using a partial least squares algorithm or a peak height algorithm.

[22] In another embodiment, the present invention relates to any one of embodiments [17] to [21], wherein the analyte comprises a perfluorocarbon gas.

[23] In another embodiment, the present invention relates to any one of embodiments [17] to [22], wherein the perfluorocarbon gas comprises perfluoropropane.

[24] In another embodiment, the present invention relates to an apparatus for quantitatively monitoring the presence of an analyte in a closed vial comprising:
1. a vial feeding mechanism;
2. a conveyor operatively associated with the vial feeding mechanism for receiving vials from the vial feeding mechanism;
3. an analyzer operatively associated with the conveyor for determining a value of a spectral property at a position within headspaces of the vials, the spectral property being dependent on analyte concentration; and
4. an indicator operatively associated with the analyzer and the conveyor for indicating vials wherein the presence of the analyte is measured quantitatively and detected as product vials, and for indicating vials wherein the quantity of analyte measured is different than the analyte in the product vials, these vials are detected as rejected vials.

[25] In another embodiment, the present invention relates to embodiment [24] further comprising a transporter operatively associated with the vial feeding mechanism for receiving vials from the vial feeding mechanism and operatively associated with the conveyor for transferring vials to the conveyor.

[26] In another embodiment, the present invention relates to any one of embodiments [24] or [25] further comprising a first vial counter operatively associated with the transporter for counting the number of vials received by the transporter.

[27] In another embodiment, the present invention relates to any one of embodiments [24] to [26] further comprising a transferrer for receiving vials from the conveyor.

[28] In another embodiment, the present invention relates to any one of embodiments [24] to [27] further comprising a reject station operatively associated with the transferrer for receiving rejected vials from the transferrer.

[29] In another embodiment, the present invention relates to any one of embodiments [24] to [28] further comprising a second vial counter operatively associated with the transferrer for counting the number of vials received by the transferrer.

[30] In another embodiment, the present invention relates to any one of embodiments [24] to [29] further comprising a sampler operatively associated with the transferrer for removing sample collection vials from the transferrer.

[31] In another embodiment, the present invention relates to any one of embodiments [24] to [30] further comprising a third vial counter operatively associated with the sampler for counting the number of vials received by the sampler.

[32] In another embodiment, the present invention relates to any one of embodiments [24] to [31] further comprising a sample collection station operatively associated with the sampler for receiving the sample collection vials from the sampler.

[33] In another embodiment, the present invention relates to any one of embodiments [24] to [32] further comprising a labeler operatively associated with the transferrer for labeling product vials received from the transferrer.

[34] In another embodiment, the present invention relates to any one of embodiments [24] to [33] wherein the analyte comprises a perfluorocarbon gas.

[35] In another embodiment, the present invention relates to embodiment [34] wherein the perfluorocarbon gas comprises perfluoropropane.

[36] In another embodiment, the present invention relates to any one of embodiments [24] to [35] further comprising a separator situated between the vials on the conveyor, such that the signal from the analyzer does not saturate the indicator as the vials are moved through the optical path of the analyzer.

[37] In another embodiment, the present invention relates to a method for quantitatively measuring an analyte in a closed vial comprising the steps of:
1. conveying a sample contained within the closed vial to an analyzer;
2. determining a value of a spectral property dependent on analyte concentration at a position within a headspace formed above the sample within the vial;

3. comparing the measured value of the spectral property with a predetermined limit criteria to determine the quantity of the analyte;
4. indicating vials wherein the desired quantity of analyte is detected as product vials and indicating vials wherein the undesired quantity of analyte is detected as rejected vials;
5. conveying the rejected vials to a rejected vial station;
6. conveying a first portion of the product vials to a sample collection station; and
7. conveying a second portion of the product vials to a labeler.

[38] In another embodiment, the present invention relates to embodiment [37] wherein the analyte comprises a perfluorocarbon gas.

[39] In another embodiment, the present invention relates to embodiment [38] wherein the perfluorocarbon gas comprises perfluoropropane.

[40] In another embodiment, the present invention relates to a method for quantitatively monitoring the presence of an analyte in a headspace of a sample vial comprising the steps of:
1. performing a first spectral analysis of an analyte contained within a headspace of a test vial, wherein the concentration of the analyte in the headspace is at a predetermined level;
2. identifying a spectral region containing an absorption peak specific for the analyte in the headspace of the test vial from the first spectral analysis;
3. determining a first intensity for the identified spectral region from the first spectral analysis;
4. performing a second spectral analysis of gas contained within a headspace of a sample vial containing a sample;
5. determining a second intensity for the identified spectral region from the second spectral analysis;
6. comparing the second intensity with the first intensity to determine the quantity of the analyte in the headspace of the sample vial.

[41] In another embodiment, the present invention relates to embodiment [40] wherein the spectral region identified is an infrared spectral region.

[42] In another embodiment, the present invention relates to any one of embodiments [40] to [41] further wherein the first and second intensities are determined from a height of the absorption peak.

[43] In another embodiment, the present invention relates to any one of embodiments [40] to [42] wherein the first and second intensities are determined from an area of the absorption peak.

[44] In another embodiment, the present invention relates to any one of embodiments [40] to [43] wherein the area of the absorption peak is determined using a partial least squares algorithm or a peak height algorithm.

[45] In another embodiment, the present invention relates to any one of embodiments [40] to [44] wherein the analyte comprises a perfluorocarbon gas.

[46] In another embodiment, the present invention relates to embodiment [45] wherein the perfluorocarbon gas comprises perfluoropropane.

[47] In another embodiment, the present invention relates to any one of embodiments [14], [17], [37], or [40] wherein the analyte comprises a gas selected from the group: fluorinated gas, fluorocarbon gas and perfluorocarbon gas.

[48] In another embodiment, the present invention relates to any one of embodiments [14], [17], [37], or [40] wherein the analyte comprises a perfluorocarbon gas selected from the group: perfluoromethane, perfluoroethane, perfluoropropane (PFP), perfluorobutane, and perfluoropentane, perfluorobutane, heptafluoropropane and mixtures thereof.

[49] In another embodiment, the present invention relates to any one of embodiments [14], [17], [37], or [40] wherein the analyte comprises a fluorinated liquid.

[50] In another embodiment, the present invention relates to any one of embodiments [14], [17], [37], or [40] wherein the analyte comprises a fluorinated liquid selected from the group consisting of: liquid perfluorocarbon and liquid perfluoroether.

[51] In another embodiment, the present invention relates to embodiment [50] wherein the fluorinated liquid is selected from the group consisting of: perfluorohexane, perfluoroheptane, perfluorooctane, perfluorononane, perfluorodecane, perfluorododecane, perfluorocyclohexane, perfluorodecalin, perfluorododecalin, perfluorooctyliodide, perfluorooctylbromide, perfluorotripropylamine, perfluorotributylamine, perfluorobutylethyl ether, bis(perfluoroisopropyl) ether and bis(perfluoropropyl) ether, and mixtures thereof.

[52] In another embodiment, the present invention relates to any one of embodiments [14], [17], [37], or [40] wherein the vial is a plastic vial capable of affording a spectral window through which specific analytes may be detected.

[56] In another embodiment, the present invention relates to any one of embodiments [14] to [16] wherein conveying the vial to the analyzer is carried out at a rate of about 150 vials per minute.

[57] In another embodiment, the present invention relates to either embodiment [24] to [36], wherein the apparatus can analyze the value of the spectral property in the vial at a speed of about 150 vials per minute.

[58] In another embodiment, the present invention relates to any one of embodiments [37] to [39] wherein conveying the vial to the analyzer is carried out at a rate of about 150 vials per minute.

It will be within the knowledge of the skilled person that some embodiments of the invention may require a spacer between the vials in the apparatus so as to prevent high light levels travelling between the vials and saturating the analyzer. In particular, the need for a spacer between the vials will depend on the speed at which the vials pass through the detector. For example, where conveying the vial to the analyzer is carried out at high speeds (e.g. at a rate of about 150 vials per minute), it is preferred that a spacer be used between the vials. Alternatively, to prevent saturation of the analyzer at high speeds a capacitor on the preamplifier of the apparatus can be adjusted to allow for faster responses from the analyzer.

A wide variety of analytes can be present in the headspace of a sample vial in accordance with the present invention, for example, fluorinated gases (that is, a gas containing one or more fluorine molecules, such as sulfur hexafluoride), fluorocarbon gases (that is, a fluorinated gas which is a fluorinated carbon or gas), and perfluorocarbon gases (that is, a fluorocarbon gas which is fully fluorinated, such as perfluoropropane and perfluorobutane). Preferably, the analyte is a perfluorocarbon gas, such as perfluoromethane, perfluoroethane, perfluoropropane (PFP), perfluorobutane, or perfluoropentane. More preferred are gases which contain more than one fluorine atom, with perfluorocarbons (that is, fully fluorinated fluorocarbons). Preferably, the perfluorocarbon gas is selected from the group consisting of perfluoromethane, perfluoroethane, perfluoropropane, perfluorobutane, perfluoropentane, perfluorocyclobutane and mixtures thereof. More preferably, the perfluorocarbon gas is perfluoropropane or perfluorobutane, with perfluoropropane being particularly preferred. Yet another preferable gas is heptafluoropropane, including 1,1,1,2,3,3,3-heptafluoropropane and its isomer, 1,1,2,2,3,3,3-heptafluoropropane. It is contemplated that mixtures of different types of gases, such as mixtures of a perfluorocarbon gas and another type of gas, such as air, can also be used in the compositions of the present invention. Other gases, including the gases exemplified above, would be readily apparent to one skilled in the art based on the present disclosure.

In yet another of its aspects, the present invention relates to the use of plastic vials in the above mentioned methods, so as to afford another spectral window wherein specific analytes may be detected. In particular, a spectral region must be determined wherein (i) the analyte has at least one absorption feature and (ii) the plastic vial has essentially no interfering absorption features. By interfering absorption features is meant absorption features which overlap the absorption feature used to identify the analyte thereby causing the detection selectivity between the analyte and the plastic vial to be compromised. Many such spectral windows (where the plastic vial has no absorption or very weak absorption) exist within the absorption regions of an analyte species. It will be further appreciated that the wavelength position and width of a specific spectral window depends directly on the specific analyte species and the specific plastic vial.

Furthermore, in yet another of its aspects, the present invention relates to methods for quantitatively measuring analyte in a sample vial, or measuring the absence or presence of the analyte in a sample vial, wherein the analyte is a fluorinated liquid. Examples of fluorinated liquids include perfluorocarbon or a liquid perfluoroether, which are liquids at the temperature of use, including, for example, perfluorohexane, perfluoroheptane, perfluorooctane, perfluorononane, perfluorodecane, perfluorododecane, perfluorocyclohexane, perfluorodecalin, perfluorododecalin, perfluorooctyliodide, perfluorooctylbromide, perfluorotripropylamine, perfluorotributylamine, perfluorobutylethyl ether, bis(perfluoroisopropyl) ether and bis(perfluoropropyl) ether.

It is to be understood that this invention covers all appropriate combinations of the particular and preferred aspects referred to herein. Additional features and embodiments of the present invention will become apparent to those skilled in the art in view of the ensuing disclosure and appended claims.

BRIEF DESCRIPTION OF THE DRAWINGS

The numerous objects and advantages of the present invention may be better understood by those skilled in the art by reference to the accompanying detailed description and the following drawings, in which.

DETAILED DESCRIPTION OF THE INVENTION

Figure 1:
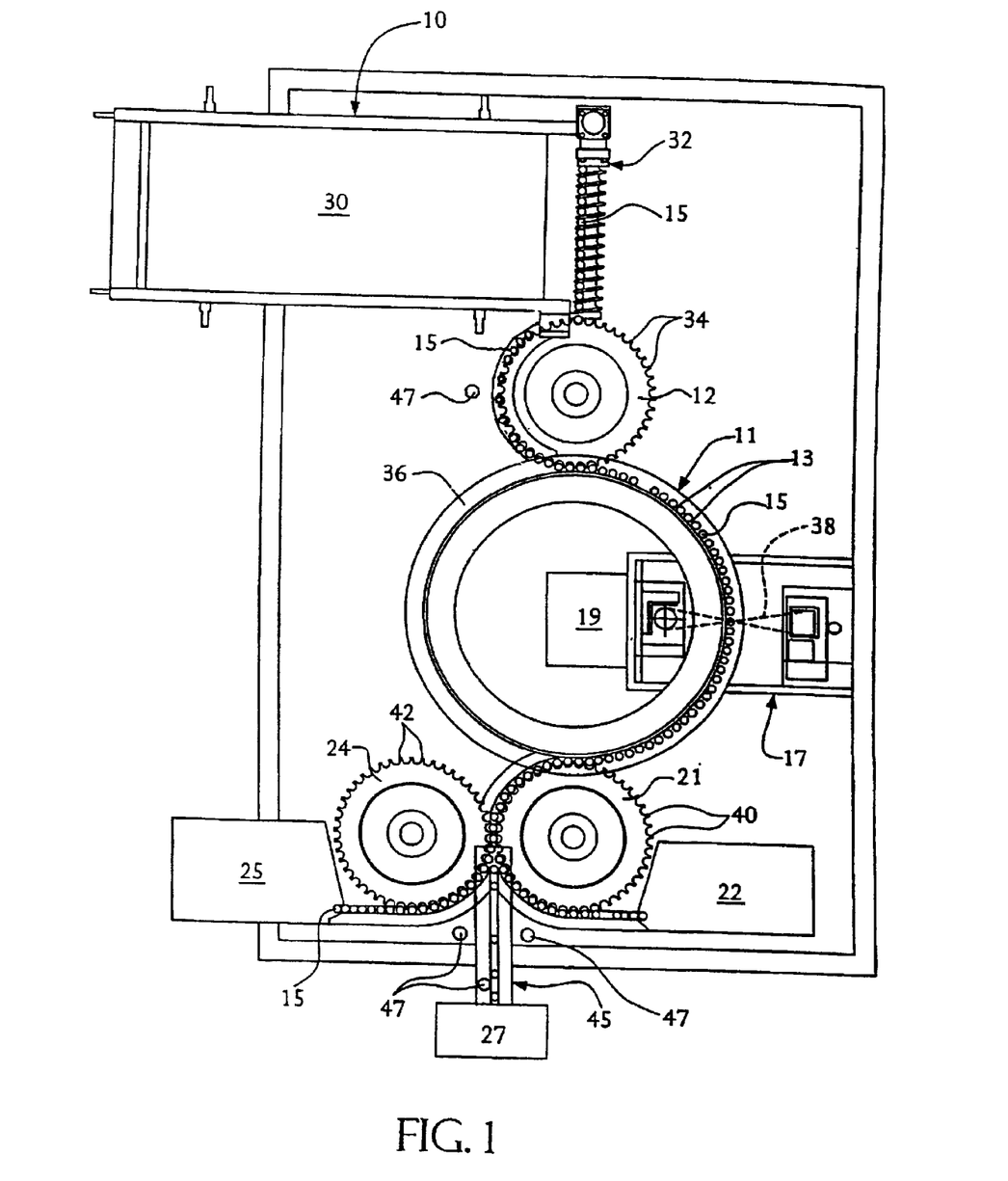
FIG. 1 is a schematic view of an apparatus in accordance with the present invention.
Figure 2:
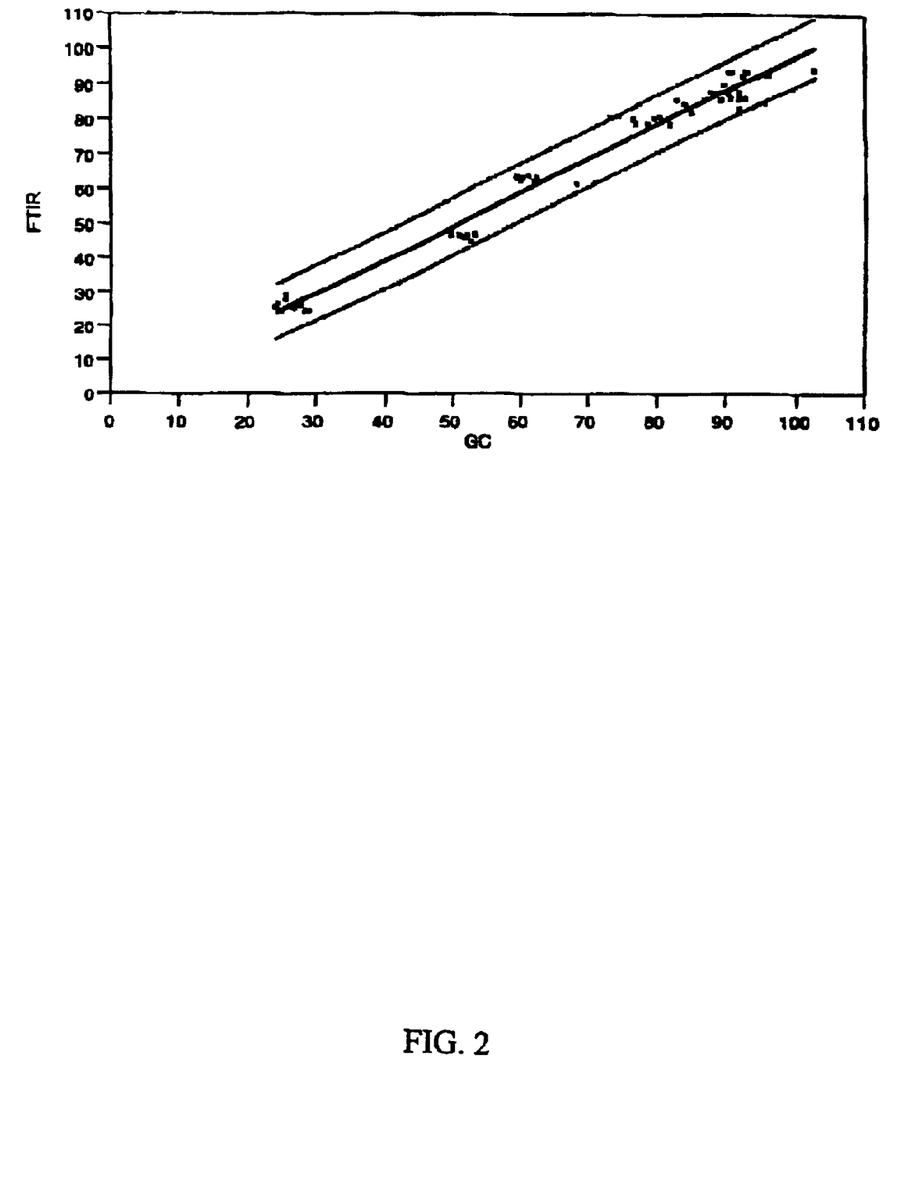
FIG. 2 represents a calibration plot comparing the analytical responses for the GC vs. FTIR on-line method.
Figure 3:
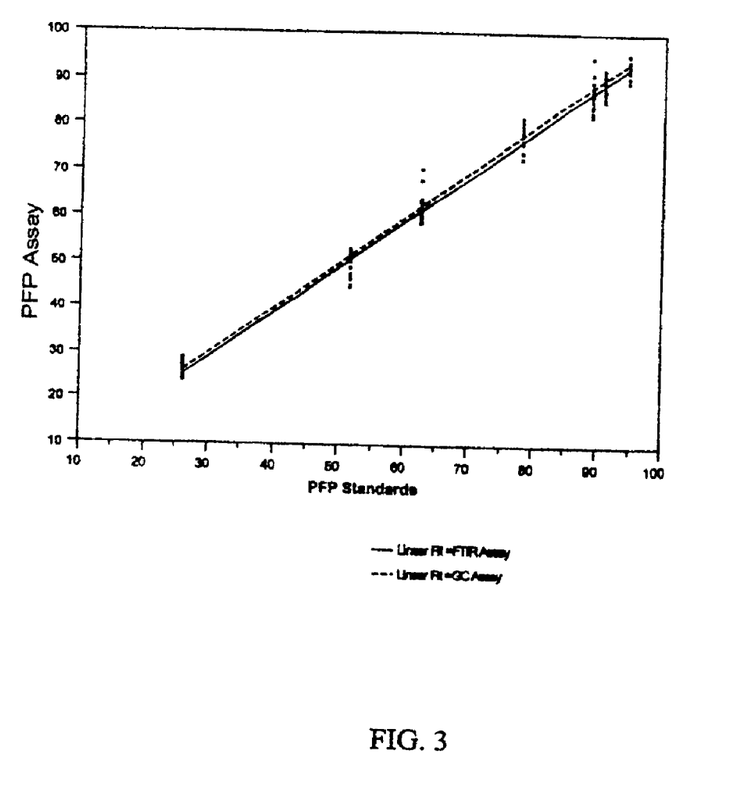
FIG. 3 represents a calibration plot comparing PFP assay values determined by FTIR online analyzer and manual GC analysis vs. the standard assay values for seven different perfluoropropane (PFP) concentrations.

An apparatus in accordance with the present invention is depicted in FIG. 1. The apparatus comprises a vial feeding mechanism 10 for feeding vials to a conveyor 11. An optional transporter 12 is positioned between the vial feeding mechanism 10 and the conveyor 11 to facilitate the positioning of vials 15 within the conveyor 11. An analyzer 17 is operatively associated with the conveyor 11 for determining a value of a spectral property at a position within headspaces of the vials 15. An indicator 19 is provided for indicating vials wherein the presence of the analyte is detected as product vials and for indicating vials wherein the absence of the analyte is detected as rejected vials. A transferrer 21 and a reject station 22 cooperate for receiving rejected vials from the conveyor 11. An optional sampler 24 and an optional sample collection station 25 are operatively associated with the transferrer 21 for removing sample collection vials from the transferrer 21 so that the sample collection vials can be removed for further analysis. Product vials are received from the transferrer 21 and labeled by an optional labeler 27. Alternatively, product vials are transferred by the transferrer 21 to a product collection station (not shown).

The vial feeding mechanism 10 comprises a vial storage compartment 30 configured to store a plurality of vials. A linear, screw conveyor 32 is associated with the vial storage compartment 30 for conveying vials, one at a time, to the transporter 12. The pitch of the screw conveyor 32 is sized so that a single vial can be loosely held between adjacent threads.

The optional transporter 12 comprises a rotatable wheel with cogs 34 that are sized and shaped to hold one vial between adjacent cogs in a loose friction fit. The transporter 12 is positioned relative to the vial feeding mechanism 10 so that vials reaching the end of the path of the vial feeding mechanism 10 are placed between adjacent cogs 34 of the transporter 12.

The conveyor 11 comprises a rotatable wheel having a track 36 along the perimeter of the conveyor 11 for receiving vials 15 from the transporter 12. The conveyor 11 is positioned relative to the transporter 12 so that vials positioned between the cogs 34 of the transporter 12 are placed along the track 36 of the conveyor 11 as the conveyor 11 and the transporter 12 counter-rotate. Toward that end, the track 36 of the conveyor 11 is at a horizontal position that overlaps the cogs 34 of the transporter 12. The conveyor 11 is positioned, however, so that the track 36 is at a vertical position that is at, or slightly below, the level of the bottom of the vials contained within the cogs 34 of the transporter 12.

The analyzer 17 is positioned relative to the conveyor 11 so that an optical path 38 associated with the analyzer 17 passes through the headspace of the vials positioned along the track 36 of the conveyor 11 as the conveyor 11 rotates to convey the vials through the analyzer 17. The conveyor 11 further comprises a separator 13 situated between the vials on the conveyor 11, such that the signal from the analyzer 17 does not saturate the indicator 19 as the vials 15 are moved through the optical path 38 of the analyzer 17. The analyzer 17 functions to determine a value of a spectral property dependent on analyte concentration. In the particular embodiment shown in FIG. 1, the analyzer 17 is a fourier transform infrared (FTIR) spectrometer capable of conducting an infrared analysis of gases contained within the headspace of the vials.

The analyzer 17 is also operatively associated with the indicator 19 for transmitting a signal indicative of the value of the measured spectral property to the indicator 19. The indicator 19 utilizes the signal to determine whether the analyte is present in the headspace of the vial by comparing the measured value with predetermined limits. Accordingly, the indicator 19 functions to determine, for each vial, the presence or absence of the analyte in the headspace of the vials. Vials which contain the analyte are indicated by the indicator 19 as corresponding to product vials. Similarly, vials which do not contain the analyte (or do not contain the desired concentration of analyte) are indicated by the indicator 19 as corresponding to rejected vials.

The transferrer 21 comprises a rotatable wheel with cogs 40 that are sized and shaped to hold one vial between adjacent cogs 40 in a loose friction fit. The transferrer 21 is positioned relative to the conveyor 11 so that vials positioned along the track 36 of the conveyor 11 are removed from the track 36 by the cogs 40 of the transferrer 21 as the transferrer 21 and the conveyor 11 counter-rotate. Toward that end, the cogs 40 of the transferrer 21 are at a horizontal position that overlaps the track 36 of the conveyor 11. The transferrer 21 is positioned, however, so that the cogs 40 of the transferrer 21 are at a vertical position that is above the level of the bottom of the vials contained along the track 36 of the conveyor 11. The reject station 22 is positioned relative to the transferrer 21 to receive vials from the transferrer 21. The reject station 22 functions to store rejected vials for later removal.

The sampler 24 comprises a rotatable wheel having cogs 42 that are sized and shaped to hold one vial between adjacent cogs 42 in a loose friction fit. The sampler 24 is positioned relative to the transferrer 21 so that vials contained between the cogs 40 of the transferrer 21 are removed from the transferrer 21 by the cogs 42 of the sampler 24 as the sampler 24 and the transferrer 21 counter-rotate. Toward that end, the cogs 42 of the sampler 24 are at a horizontal position that overlaps the cogs 40 of the transferrer 21. The sampler 24 is positioned, however, so that the cogs 42 of the sampler 24 are at a vertical position that is displaced from the cogs 40 of the transferrer 21, so that the sampler 24 holds the vials at a position that is vertically displaced from the position where the vials are held by the transferrer 21. The sampler 24 collects vials from the transferrer 21 at a predetermined rate. In one embodiment, the sampler 24 collects vials at a predetermined interval (e.g., every $100^{th}$ vial). Alternatively, the sampler 24 collects vials randomly but at a predetermined rate (e.g., 2 out of every hundred vials).

The selected product vials are removed from the transferrer 21 by the sampler 24 and then stored by the optional sample collection station 25. The selected product vials are removed manually from the sample collection station 25 and subjected to additional testing including, for example, safety or quality assurance testing.

Product vials which are not sampled by the sampler are transferred to the labeler 27 or other similar machine designed to prepare the vials for sale or shipment. The labeler 27 is operatively associated with the transferrer 21 via, for example, a linear conveyor 45. Alternatively, product vials are transferred by the transferrer to a product collection station.

One or more optional counters 47 are provided to keep account of the number of vials processed by the apparatus. For example, counters 47 are optionally associated with the transporter 12, the transferrer 21, the linear conveyor 45, and/or the sampler 24 for determining the number of vials that have been processed by the transporter 12, the transferrer 21 and the sampler 24, respectively. The counters 47 can count the number of vials using any of a number of conventional techniques, including optical sensing methods.

In operation, samples are contained within closed vials and the closed vials are placed within the vial storage compartment 30 of the apparatus. The vials are then individually conveyed to the transporter 12 by the vial feeding mechanism 10. The transporter 12 is rotated to transport the vials to the conveyor 11 and simultaneously receive additional vials from the vial feeding mechanism 10. The conveyor 11 is continually rotated to receive vials from the transporter 12 and simultaneously convey the vials through the analyzer 17. As the vials pass through the analyzer 17, the value of a spectral property dependent on analyte concentration is determined at a position within the headspace formed above the sample within the vial. A signal that is representative of the measured value of the spectral property is transmitted by the analyzer 17 to the indicator 19 where it is compared to predetermined limit criteria to determine the presence or absence of analyte in the headspace. Since the indicator 19 is also operatively associated with the conveyor 11, the indicator 19 also functions to indicate vials wherein the presence of the analyte is detected as product vials and to indicate vials wherein the absence of the analyte is detected as rejected vials. As the conveyor 11 continues to rotate, the vials are transferred from the conveyor 11 to the rotating transferrer 21. The transferrer 21 transports the vials to the sampler 24. The sampler 24 removes a portion of the product vials from the transferrer 21 and transfers those vials to the sample collection station 25. The transferrer 21 then transports the remaining vials to the conveyor 45 associated with the labeler 27. The conveyor 45 associated with the labeler 27 removes the remaining product vials from the transferrer 21 and conveys them to the labeler 27. At this point, the vials remaining in the transferrer 21 are only the rejected vials, which are transferred by the transferrer 21 to the rejected vial station 22.

EXAMPLES

An apparatus in accordance with the present invention and as depicted in FIG. 1 was used to detect the presence or absence of perfluoropropane (PFP) in sealed silica glass vials containing a lipid-containing suspension phase and a perfluoropropane gas phase. The apparatus detected the PFP using a fourier transform infrared (FTIR) Michelson analyzer (BOMEM, Inc., Quebec City, Quebec, Canada; Model No. MB 104). Validation tests were conducted to examine four method parameters: analyte specificity, limits determination, accuracy and robustness.

Analyte Specificity

The identifying spectral absorption bands for PFP are in the mid-infrared to far-infrared regions (see, Catalog of Infrared Spectral Data, American Petroleum Institute, Research project 44, Chemical Thermodynamic Properties Center, Texas A.M. University, College Station, Texas; Serial No. 981). Although silica glass vials are not ideal optical cells for spectrophotometric analysis in the mid- to far-infrared regions, silica glass does afford a restricted window for observing compounds in a small portion of the mid-infrared region between about 2800 $cm^{-1}$ and about 2400 $cm^{-1}$.

Experiments were conducted in which PFP gas standards conatined within infrared gas cells with KBr windows were spectrally scanned to identify adsorption peaks that are unique to PFP and that could be detectable through a silica glass vial. Sealed silica glass vials containing either PFP gas or air in the headspace were subsequently scanned to confirm the identification of the PFP peaks.

Comparison of the mid-infrared scans for the KBr and glass vial samples identified three absorption peaks as being specific for the PFP analyte, as shown in Table 1. The peaks at 2630 cm$^{-1}$ and 2415 cm$^{-1}$ were the two largest peaks identified which change the most in peak height and area as a function of PFP concentration.

TABLE 1

| Sample | IR Spectral Peaks (cm$^{-1}$) |
|---|---|
| IR gas cell with PFP | 2630, 2575, 2510, 2451, 2415 |
| Glass vial with PFP | 2631, 2575, 2510, 2450, 2415 |
| Glass vial with air | 2545, 2510, 2455 |

The two identified absorption peaks for PFP are well separated from piotential ambient interferences of H$_2$O or CO$_2$, which have known absorption bands at 3655, 3756, and 1956 cm$^{-1}$ (H$_2$O) and 2350 cm$^{-1}$ (CO$_2$).

The specificity of the identified PFP peaks was further examined as to potential interference of the lipid-containing suspension phase. In this study, twenty sealed vials were coated with the lipid-containing suspension phase on the interior surface of the vial. Ten of the vials contained PFP gas in the headspace, while the other ten vials contained air in the headspace. Each of the twenty vials was then tested for the presence or absence of PFP in the headspace. The data of Table 2 show that the lipid-containing suspension phase does not interfere with infrared detection of PFP in the vial headspace.

TABLE 2

| Sample | Vial with PFP[a] | Vial with air[b] |
|---|---|---|
| 1 | Pass | Failed |
| 2 | Pass | Failed |
| 3 | Pass | Failed |
| 4 | Pass | Failed |
| 5 | Pass | Failed |
| 6 | Pass | Failed |
| 7 | Pass | Failed |
| 8 | Pass | Failed |
| 9 | Pass | Failed |
| 10 | Pass | Failed |

[a]Pass = greater than 55% PFP in the vial headspace
[b]Failed = less than 55% PFP in the vial headspace Limits Determination The limits determination criteria for the apparatus was set by the ability of the apparatus to discriminate between a vial containing PFP in the headspace (at a concentration of 80% or greater) and one containing only air. The ability of the apparatus to distinguish between these two conditions is a function of the goodness of fit between the infrared signal for a sample at a known concentration and that predicted by a calibration equation.

Two methods for calculating the correlation between the infrared signals and analyte concentrations were used. The first method is a linear regression calculation using two factors such as changes in absorption peak height at a given wavelength and the known concentration of the analyte. The second method involves using a partial least squares (PSL) modeling algorithm in which all of the spectral data points for the spectral region spanning the absorption peak are iteratively fit to a set of linear regression equations as a function of analyte concentration (see, for example, H. Martens & T. Naes, "Multivariate Calibration" (1989) John Wiley & Sons, p. 188 ff.).

Each of the calibration models was tested using infrared spectral data obtained for ten sealed vials having each of the following average headspace PFP concentrations: 0% (air), 43.6%, 44.1%, 68.5%, and 81%. The headspace PFP concentrations in the sealed vials were confirmed using gas chromotography/thermal conductivity detection (GC/TCD). The spectral data for each of the ten vials having the same headspace PFP concentration was then analyzed to determine the standard deviation and the pooled standard error. The results which are given in Table 3 show that, although both methods provide a reasonable calibration, the PLS regression method has somewhat lower standard deviations and a smaller pooled standard error value.

TABLE 3

| | Standard Deviation[a] | |
|---|---|---|
| PFP Concentration (%) | Peak Height Regression | PLS Regression |
| 0 | 2.3 | 3.1 |
| 43.6 | 2.4 | 1.6 |
| 44.1 | 3.3 | 3.4 |
| 68.5 | 4.9 | 2.4 |
| 81 | 3.4 | 2.5 |
| Pooled Standard Error[b] | 1.07 | 0.85 |

[a]N = 10 determinations at each PFP concentration

[b]Pooled Standard Error = $\sqrt{\dfrac{\sum_{i=1}^{i}\left(\dfrac{s_i^2}{n_i}\right)}{i}}$, wherein $s_i$ is the standard deviation of the response for concentration "I," "I" = 1, 2, . . . 5, and $n_i$ is the number of determinations for concentration "i".

The analytical precisions of the peak height and the PLS methods were also evaluated by comparing the variability in measurements obtained for a single vial. In this study, ten measurements using both methods of analysis were recorded for a first vial containing 80% PFP and a second vial containing only air in the headspace (i.e., a headspace PFP concentration of 0%). The spectral data for each of the ten vials having the same headspace PFP concentration was then analyzed to determine the standard deviation. The results which are given in Table 4 show that, although both methods provide reasonable precision, the PLS regression method has somewhat lower standard deviations.

TABLE 4

| | Standard Deviation[a] | |
|---|---|---|
| PFP Concentration (%) | Peak Height Regression | PLS Regression |
| 80 | 3.18 | 1.94 |
| 0(Air) | 1.53 | 1.18 |

[a]N = 10 determinations at each PFP concentration

Using the PLS regression method, limits were then set to insure a low probability of having either a false positive or false negative result. Historically, the concentration of PFP in the headspace of product vials of contrast agent has ranged from the low 80% level to values in the high 90% level. The identification (I.D.) limits for the positive PFP samples were therefore benchmarked to the compiled calibration data for the 80% PFP vial samples. Correspondingly, the data for the air filled sample vials were used to evaluate the negative I.D. limits. Operating then from the mean reported value for the 80% PFP standards, the PFP positive I.D. test results were bracketed between the 55% and 105% PFP calibration values. All values reported outside this range would be reported as negative I.D. test results. Using these limits for identifying PFP in the sample vials, a shift of 46 standard deviations would be required to have a false positive identification of an air filled vial. Likewise, a shift of 13 standard deviations would be needed to have a false negative identification of an 80% PFP filled vial. In both cases, the shifts in standard deviations translate into a probability of less than 1 chance in $1\times10^{30}$ events to have a false positive or negative result.

Accuracy

Having established the limits determination parameters, the accuracy of the apparatus was assessed as to its ability to discern between product vials containing PFP and those with air in the headspace. Six hundred vials containing the lipid-containing suspension phase were randomly collected from different production lots. The collected vials were then segregated into two groups of three hundred vials (Groups A and B). For two hundred vials from each of the two groups, the headspace gas was replaced with air. The two groups of 300 vials now contained a total of 200 vials with air in the headspace and 100 vials with PFP in the headspace.

Two random ordered testing lists for air and PFP headspace vials were generated. Vials in each group were the numerically labeled according to one of the two sample testing lists, to create a blinded sample population for the analysts. Three analysts tested the two blinded sample populations over a period of three days. The test results as a function of analyst and days are consistent, as shown in the data of Table 5.

TABLE 5

| Conditions | | Group A | | Group B | |
|---|---|---|---|---|---|
| Analyst | Day | Positive | Negative | Positive | Negative |
| 1 | 1 | 95 | 205 | — | — |
| 1 | 2 | — | — | 100 | 200 |
| 2 | 2 | 95 | 205 | — | — |
| 3 | 3 | — | — | 100 | 200 |

As shown in Table 5, a 100% identification of vials containing PFP or air in the headspaces was achieved fro Group B. Five of the vials in Group A, however, which were assigned as containing PFP in the headspace were identified by the apparatus as containing air in the headspace. Subsequent analysis of those five vials using GC/TCD confirmed that those vials contained less than 55% PFP in the headspace. Since the limits detection was set to reject vials containing less than 55% PFP in the headspace, the apparatus correctly identified those vials. In particular, three of those vials contained less than 1% PFP in the headspace, while one vial contained about 7% and one vial contained about 20%. The test results therefore satisfy an accuracy criteria of zero false positive results for 800 tested vials containing air in the headspace.

Robustness

The robustness of the apparatus was evaluated with respect to defects or flaws in the state or condition of the sample vial. Conditions such as abuse of the sample or imperfections in the glass vial were considered significant if they impede or prevented the correct identification of the product. Ten product vials containing PFP in the headspace and ten product vials with air in the headspace were modified to simulate sample abuse conditions that could occur during routine use of the vials. These conditions ranged from covering the outer surface of the vial with fingerprints, a thin layer of hand cream, liquid detergent, powder from rubber gloves and a paper label blocking the headspace. The exterior surfaces of two glass vials with PFP and two vials with air headspace were scratched to simulate imperfection in the glass. Two vials with PFP and two with air in the headspace were also shaken by hand to produce froth in the headspace. A total of twenty vials were tested for PFP content in the headspace.

The results from the robustness study, as shown in Table 6, indicate that two conditions (i.e., froth and paper labels blocking the optical path) can produce a false negative result, while the five other test conditions have no effect on the analysis. None of the seven test conditions produced a false positive result.

TABLE 6

| Sample Vial Condition | PFP in Headspace | Air in Headspace |
|---|---|---|
| fingerprints | Pass | Fail |
| fingerprints | Pass | Fail |
| hand cream | Pass | Fail |
| detergent | Pass | Fail |
| powder | Pass | Fail |
| scratches | Pass | Fail |
| scratches | Pass | Fail |
| froth | Pass | Fail |
| froth | Fail | Fail |
| paper label | Fail | Fail |

Quantitative Analysis:

Quantitative analysis of the analyte in the vials can be carried out using methods similar to those described herein. The results shown in FIGS. 2 and 3, indicate a good correlation between the methods and accuracy to the reference concentration values, since all the calibration slopes approach a value of 1 and the "y-intercepts" are less than 0.5. The presented data supports a claim that the FTIR on-line method is quantitative over a PFP concentration range of 30% to 100%.

Those skilled in the art will appreciate that numerous changes and modifications may be made to the preferred embodiments of the invention and that such changes and modifications may be made without departing from the spirit of the invention. For example, the apparatus and methods of the present invention can be used to monitor the presence or absence of a variety of gases in the headspace of a vial provided that a spectral property, specific for the selected gas and indicative of the concentration of the selected gas, can be identified and measured. In addition, it is within the scope of the present invention to modify the apparatus and methods to utilize different analytical techniques, for example, nuclear magnetic resonance (NMR) spectroscopy and, in particular, $F^{19}$-NMR spectroscopy; vibrational spectroscopy, in particular, Infra red and Raman; electronic spectroscopy, in particular, ultraviolet spectroscopy; and refractive index spectroscopy (e.g. X-ray crystallography, x-ray fluorescence, or fluorescence). Also, it is within the scope of the present invention to modify the apparatus and methods to utilize either light transmission mode or light reflectance mode. It is therefore intended that the appended claims cover all equivalent variations as fall within the true scope and spirit of the invention.

What is claimed is:

1. An apparatus for monitoring the presence of an analyte in a closed vial comprising:

(a) a vial feeding mechanism;

(b) a conveyor operatively associated with the vial feeding mechanism for receiving vials from the vial feeding mechanism;

(c) an analyzer operatively associated with the conveyor for determining a value of a spectral property between from about 2800 cm$^{-1}$ and about 2400 cm$^{-1}$ at a position within headspaces of the vials, the spectral property being dependent on analyte concentration; and (d) an indicator operatively associated with the analyzer and the conveyor for indicating vials wherein the presence of the analyte is detected as product vials and for indicating vials wherein the absence of the analyte is detected as rejected vials.

2. The apparatus of claim 1 comprising a transporter operatively associated with the vial feeding mechanism for receiving vials from the vial feeding mechanism and operatively associated with the conveyor for transferring vials to the conveyor.

3. The apparatus of claim 2 comprising a first vial counter operatively associated with the transporter for counting the number of vials received by the transporter.

4. The apparatus of claim 1 comprising a transferrer for receiving vials from the conveyor.

5. The apparatus of claim 4 comprising a reject station operatively associated with the transferrer for receiving rejected vials from the transferrer.

6. The apparatus of claim 4 comprising a second vial counter operatively associated with the transferrer for counting the number of vials received by the transferrer.

7. The apparatus of claim 4 comprising a sampler operatively associated with the transferrer for removing sample collection vials from the transferrer.

8. The apparatus of claim 7 comprising a third vial counter operatively associated with the sampler for counting the number of vials received by the sampler.

9. The apparatus of claim 7 comprising a sample collection station operatively associated with the sampler for receiving the sample collection vials from the sampler.

10. The apparatus of claim 4 comprising a labeler operatively associated with the transferrer for labeling product vials received from the transferrer.

11. The apparatus of claim 1 wherein the analyte comprises a perfluorocarbon gas.

12. The apparatus of claim 11 wherein the perfluorocarbon gas comprises perfluoropropane.

13. The apparatus of claim 1 further comprising a separator situated between the vials on the conveyor, such that the signal from the analyzer does not saturate the indicator as the vials are moved through the optical path of the analyzer.

14. A method for monitoring the presence of an analyte in a closed vial comprising the steps of:

(a) conveying a sample contained within the closed vial to an analyzer;

(b) determining a value of a spectral property between about 2800 cm$^{-1}$ and about 2400 cm$^{-1}$ dependent on analyte concentration at a position within a headspace formed above the sample within the vial;

(c) comparing the measured value of the spectral property with a predetermined limit criteria to determine the presence of the analyte;

(d) indicating vials wherein the presence of the analyte is detected as product vials and indicating vials wherein the absence of the analyte is detected as rejected vials;

(e) conveying the rejected vials to a rejected vial station;

(f) conveying a first portion of the product vials to a sample collection station; and (g) conveying a second portion of the product vials to a labeler.

15. The method of claim 14 wherein the analyte comprises a perfluorocarbon gas.

16. The method of claim 15 wherein the perfluorocarbon gas comprises perfluoropropane.

17. The method according to claim 14, wherein the analyte comprises a gas selected from the group: fluorocarbon gas and perfluorocarbon gas.

18. The method according to claim 14, wherein the analyte comprises a perfluorocarbon gas selected from the group: perfluoromethane, perfluoroethane, perfluoropropane (PFP), perfluorobutane, and perfluoropentane, perfluorobutane, heptafluoropropane and mixtures thereof.

19. The method according to claim 14, wherein the sample comprises a fluorinated liquid.

20. The method according to claim 19, wherein the fluorinated liquid is selected from the group consisting of: perfluorohexane, perfluoroheptane, perfluorooctane, perfluorononane, perfluorodecane, perfluorododecane, perfluorocyclohexane, perfluorodecalin, perfluorododecalin, perfluorooctyliodide, perfluorooctylbromide, perfluorotripropylamine, perfluorotributylamine, perfluorobutylethyl ether, bis(perfluoroisopropyl) ether and bis(perfluoropropyl) ether, and mixtures thereof.

21. The method according to claim 14, wherein the sample comprises a fluorinated liquid selected from the group consisting of: liquid perfluorocarbon and liquid perfluoroether.

22. The method according to claim 14, wherein the vial is a plastic vial capable of affording a spectral window through which specific analytes may be detected.

23. A method for monitoring the presence of an analyte in a headspace of a sample vial comprising the steps of:

(a) performing a first spectral analysis between about 2800 cm$^{-1}$ and about 2400 cm$^{-1}$ of an analyte contained within a headspace of a test vial, wherein the concentration of the analyte in the headspace is at a predetermined level;

(b) identifying a spectral region containing an absorption peak specific for the analyte in the headspace of the test vial from the first spectral analysis;

(c) determining a first intensity for the identified spectral region from the first spectral analysis;

(d) performing a second spectral analysis between about 2800 cm$^{-1}$ and about 2400 cm$^{-1}$ of gas contained within a headspace of a sample vial containing a sample;

(e) determining a second intensity for the identified spectral region from the second spectral analysis;

(f) comparing the second intensity with the first intensity to determine the presence of the analyte in the headspace of the sample vial.

24. The method of claim 23 wherein the first and second intensities are determined from a height of the absorption peak.

25. The method of claim 23 wherein the first and second intensities are determined from an area of the absorption peak.

26. The method of claim 25 wherein the area of the absorption peak is determined using a partial least squares algorithm of the spectral response or a peak height algorithm.

27. The method of claim 23 wherein the analyte comprises a perfluorocarbon gas.

28. The method of claim 27 wherein the perfluorocarbon gas comprises perfluoropropane.

29. An apparatus for quantitatively monitoring the presence of an analyte in a closed vial comprising:

(a) a vial feeding mechanism;
(b) a conveyor operatively associated with the vial feeding mechanism for receiving vials from the vial feeding mechanism;
(c) an analyzer operatively associated with the conveyor for determining a value of a spectral property between about 2800 cm$^{-1}$ and about 2400 cm$^{-1}$ at a position within headspaces of the vials, the spectral property being dependent on analyte concentration; and
(d) an indicator operatively associated with the analyzer and the conveyor for indicating vials wherein the presence of the analyte is measured quantitatively and detected as product vials, and for indicating vials wherein the quantity of analyte measured is different than the analyte in the product vials, these vials are detected as rejected vials.

30. The apparatus of claim 29 comprising a transporter operatively associated with the vial feeding mechanism for receiving vials from the vial feeding mechanism and operatively associated with the conveyor for transferring vials to the conveyor.

31. The apparatus of claim 30 comprising a first vial counter operatively associated with the transporter for counting the number of vials received by the transporter.

32. The apparatus of claim 29 comprising a transferrer for receiving vials from the conveyor.

33. The apparatus of claim 32 comprising a reject station operatively associated with the transferrer for receiving rejected vials from the transferrer.

34. The apparatus of claim 32 comprising a second vial counter operatively associated with the transferrer for counting the number of vials received by the transferrer.

35. The apparatus of claim 32 comprising a sampler operatively associated with the transferrer for removing sample collection vials from the transferrer.

36. The apparatus of claim 35 comprising a third vial counter operatively associated with the sampler for counting the number of vials received by the sampler.

37. The apparatus of claim 35 comprising a sample collection station operatively associated with the sampler for receiving the sample collection vials from the sampler.

38. The apparatus of claim 32, comprising a labeler operatively associated with the transferrer for labeling product vials received from the transferrer.

39. The apparatus of claim 29 wherein the analyte comprises a perfluorocarbon gas.

40. The apparatus of claim 39 wherein the perfluorocarbon gas comprises perfluoropropane.

41. The apparatus of claim 39 further comprising a separator situated between the vials on the conveyor, such that the signal from the analyzer does not saturate the indicator as the vials are moved through the optical path of the analyzer.

42. A method for quantitatively measuring an analyte in a closed vial comprising the steps of:
(a) conveying a sample contained within the closed vial to an analyzer;
(b) determining a value of a spectral property between about 2800 cm$^{-1}$ and about 2400 cm$^{-1}$ dependent on analyte concentration at a position within a headspace formed above the sample within the vial;
(c) comparing the measured value of the spectral property with a predetermined limit criteria to determine the quantity of the analyte;
(d) indicating vials wherein the desired quantity of analyte is detected as product vials and indicating vials wherein the undesired quantity of analyte is detected as rejected vials;
(e) conveying the rejected vials to a rejected vial station;
(f) conveying a first portion of the product vials to a sample collection station; and
(g) conveying a second portion of the product vials to a labeler.

43. The method of claim 42 wherein the analyte comprises a perfluorocarbon gas.

44. The method of claim 43 wherein the perfluorocarbon gas comprises perfluoropropane.

45. A method for quantitatively monitoring the presence of an analyte in a headspace of a sample vial comprising the steps of:
(a) performing a first spectral analysis between about 2800 cm$^{-1}$ and about 2400 cm$^{-1}$ of an analyte contained within a headspace of a test vial, wherein the concentration of the analyte in the headspace is at a predetermined level;
(b) identifying a spectral region containing an absorption peak specific for the analyte in the headspace of the test vial from the first spectral analysis;
(c) determining a first intensity for the identified spectral region from the first spectral analysis;
(d) performing a second spectral analysis between about 2800 cm$^{-1}$ and about 2400 cm$^{-1}$ of gas contained within a headspace of a sample vial containing a sample;
(e) determining a second intensity for the identified spectral region from the second spectral analysis; and
(f) comparing the second intensity with the first intensity to determine the quantity of the analyte in the headspace of the sample vial.

46. The method of claim 45 wherein the first and second intensities are determined from a height of the absorption peak.

47. The method of claim 45 wherein the first and second intensities are determined from an area of the absorption peak.

48. The method of claim 47 wherein the area of the absorption peak is determined using a partial least squares algorithm of the spectral response or a peak height algorithm.

49. The method of claim 45 wherein the analyte comprises a perfluorocarbon gas.

50. The method of claim 49 wherein the perfluorocarbon gas comprises perfluoropropane.

* * * * *

UNITED STATES PATENT AND TRADEMARK OFFICE
CERTIFICATE OF CORRECTION

PATENT NO.     : 6,943,692 B2
DATED          : September 13, 2005
INVENTOR(S)    : James Castner, Luc Boudreau and Allan Rilling It is certified that error appears in the above-identified patent and that said Letters Patent is hereby corrected as shown below:

<u>Title page,</u>
Item [75], should read:
-- [75] Inventors: James Castner, Groton, MA (US); Luc Boudreau, Val Belair; Allan Rilling, Les Saules, both of Canada --.

Signed and Sealed this

Fourth Day of April, 2006

JON W. DUDAS
*Director of the United States Patent and Trademark Office*